(12) United States Patent
Palmerton et al.

(10) Patent No.: US 9,164,500 B2
(45) Date of Patent: Oct. 20, 2015

(54) METHOD AND DEVICE FOR REMOTE CONTROL OF AN APPARATUS

(75) Inventors: Christopher A. Palmerton, Williamsville, NY (US); Samantha Bonano, Williamsville, NY (US); Daniel R Palmerton, Elma, NY (US); Gregory J. Pepe, Lancaster, NY (US); Anthony L Lizauckas, III, Williamsville, NY (US); Kyrylo Shvetsov, Tonawanda, NY (US); William J Kellner, Amherst, NY (US); Michael J. Miller, West Seneca, NY (US)

(73) Assignee: Buffalo Filter LLC, Lancaster, NY (US)

(*) Notice: Subject to any disclaimer, the term of this patent is extended or adjusted under 35 U.S.C. 154(b) by 587 days.

(21) Appl. No.: 13/348,630

(22) Filed: Jan. 11, 2012

(65) Prior Publication Data

US 2012/0286179 A1 Nov. 15, 2012

Related U.S. Application Data

(60) Provisional application No. 61/431,492, filed on Jan. 11, 2011, provisional application No. 61/579,937, filed on Dec. 23, 2011.

(51) Int. Cl.
*G05B 11/01* (2006.01)
*G05B 19/042* (2006.01)
*A61M 1/00* (2006.01)
*G01F 15/00* (2006.01)

(52) U.S. Cl.
CPC .......... *G05B 19/0423* (2013.01); *A61M 1/0031* (2013.01); *G01F 15/001* (2013.01); *G01F 15/005* (2013.01); *G05B 2219/25312* (2013.01)

(58) Field of Classification Search
CPC ............. A61B 2218/008; A61B 18/14; A61B 2218/007; A61B 18/20; A61B 18/00; F21V 33/0068; F21V 7/0091
See application file for complete search history.

(56) References Cited

U.S. PATENT DOCUMENTS

| 4,420,831 | A | * | 12/1983 | Hackett | 370/481 |
| 5,675,323 | A | * | 10/1997 | Ho | 340/5.6 |
| 6,154,544 | A | * | 11/2000 | Farris et al. | 380/262 |
| 6,441,723 | B1 | * | 8/2002 | Mansfield et al. | 340/538.11 |
| 6,680,673 | B1 | * | 1/2004 | Wong | 340/12.27 |
| 2006/0254371 | A1 | * | 11/2006 | Shiloni et al. | 73/864.34 |
| 2008/0027586 | A1 | * | 1/2008 | Hern et al. | 700/284 |
| 2008/0030311 | A1 | * | 2/2008 | Dayan et al. | 340/435 |
| 2010/0171588 | A1 | * | 7/2010 | Chutorash et al. | 340/5.71 |

* cited by examiner

*Primary Examiner* — Kerri McNally
*Assistant Examiner* — Renee Dorsey
(74) *Attorney, Agent, or Firm* — Phillips Lytle LLP

(57) ABSTRACT

A remotely activatable valve unit having: an inlet port; an exit port; an electronically activatable valve configured and arranged between the inlet port and the exit port; a receiver having an output; and a controller configured to operate the valve as a function of the receiver output. The exit port may be configured to attach to a vacuum means or to a wall vacuum.

16 Claims, 8 Drawing Sheets

METHOD AND DEVICE FOR REMOTE CONTROL OF AN APPARATUS

CROSS-REFERENCE TO RELATED APPLICATIONS

The present application claims the benefit of U.S. Provisional Application No. 61/431,492, filed Jan. 11, 2011; and U.S. Provisional Application No. 61/579,937, filed Dec. 23, 2011; each of which are hereby incorporated by reference in their entirety.

BACKGROUND OF THE INVENTION

The present invention relates generally to remote activation of devices, and, more specifically, to a remote activation device for a medical vacuum.

BRIEF SUMMARY OF THE INVENTION

With reference to the corresponding parts portions or surfaces of the disclosed embodiment, merely for the purposes of illustration and not by way of limitation, the present embodiment provides a remotely activatable valve unit having: an inlet port; an exit port; an electronically activatable valve configured and arranged between the inlet port and the exit port; a receiver having an output; and a controller configured to operate the valve as a function of the receiver output. The exit port may be configured to attach to a vacuum means or to a wall vacuum.

In another aspect, the unit may further have a liquid exit port. The valve may be a solenoid valve and may have a biased default position. The biased default position may be a closed position.

The receiver may be an input wire. Alternatively, the receiver may be a radio-frequency sensor and/or may be configured to measure a radio-frequency signal across a narrow frequency range. The frequency range may be centered at about 13.56 megahertz.

In another aspect, the receiver may be a current sensor. The current sensor may be arranged in series between a power supply and an electrosurgical device. The current sensor may be electrically isolated from a current flow it may be configured to sense. The current sensor may be a hall effect sensor.

In yet another aspect, the receiver may be a acoustic sensor. The acoustic sensor may be configured and arranged to narrowly sense a sound frequency produced by an electrosurgical power unit.

The controller may be configured to open the valve when the receiver output is greater than a first threshold, and close the valve when the receiver output is less than the first threshold. The controller may be configured to open the valve when a time average of the receiver output is greater than a first threshold. The controller may be configured to calculate a frequency range of the receiver output. The controller may be configured to open the valve as a function of a time delay threshold. The controller may be configured to open the valve when the receiver output is greater than a first threshold for a duration of time greater than a time delay. The controller may be configured to keep the valve open for a second time delay before closing the valve when the receiver output drops below a first threshold.

In another aspect, the unit may also comprise a filter and/or a canister for collecting liquid.

In another aspect, a remote control unit is provided comprising: an receiver having an output; an output control line for controlling a device; a threshold setting button; a threshold parameter storage; a controller, configured to store a threshold parameter into the threshold parameter storage when the threshold setting button may be depressed, the threshold parameter being a function of the receiver output; and in which the controller is configured to produce a signal on the output control line as a function of the receiver output and the threshold parameter storage.

The receiver may be an RF receiver, and may be a Bluetooth, or wifi (e.g. IEEE 802.11 transceiver. The receiver may be an acoustic receiver.

The output control line may be a digital wire whereby a first voltage on the output control line may be used to identify when the device is turned on and a second voltage on the output control line may be used to identify when the device is turned off. The RF receiver may comprise an antenna. The antenna may be an integrated antenna.

The unit may further comprise a delay parameter. The controller may be configured to produce a signal on the output control line as a function of the delay parameter. The controller may be configured and arranged such that when the threshold setting button may be depressed, the controller sets the delay parameter as a function of a duration of time that the threshold setting button is depressed.

The unit may further comprise a logic level parameter used to designate whether a high voltage on the output control line designates an on or an off command to the device. The controller may be configured and arranged to debounce the RF receiver output. The unit may further comprise a transistor for amplifying the RF receiver output, and/or a channel for retaining a current carrying wire. The channel may be configured to hold a plurality of wires.

In another aspect, a remote control unit is provided comprising: a receiver having an output; an output control line for controlling a device; a threshold parameter storage; an integrated antenna; a controller; wherein the controller may be configured to produce a signal on the output control line as a function of the receiver output and the threshold parameter storage.

DETAILED DESCRIPTION OF THE INVENTION

Figure 1:
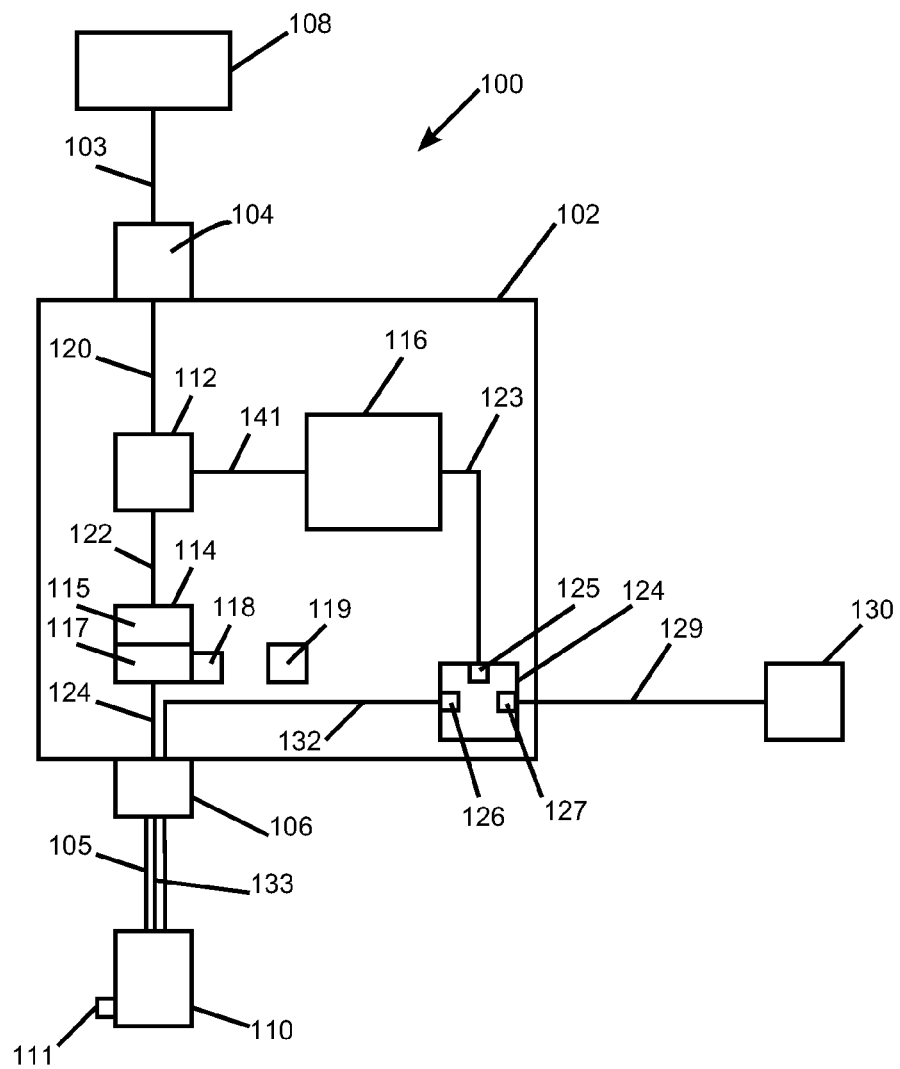
FIG. 1 shows a schematic view of a first embodiment.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

First Embodiment

Structure

Referring now to the drawings, FIG. 1 discloses first embodiment 100 of a device for remotely controlling a medical vacuum source. Embodiment 100 comprises housing 102, outlet port 104, and inlet port 106. Housing 102 is made of metal. The metal surface is nonporous and thus easily disinfectable. Other materials such as plastic may be used to construct housing 102. Outlet port 104 contains an adapter for creating an airtight connection to standard vacuum tubing 103 and connecting to vacuum source 108. Outlet port 104's adapter forms an air-tight seal through compressively engaging with tubing 103. Similarly, inlet port 106 contains an adapter for creating an air-tight seal with standard tubing for connecting to medical suction apparatus 110. A Luer-Lock or other style adapter may alternatively be used for the inlet and outlet port adapters.

Embodiment 100 contains activatable valve 112 arranged within housing 102. A first end of valve 112 connects to outlet port 104 through tube 120. Valve 112 is connected to controller 116 through control line 141, which controls the extent valve 112 is open. Activatable valve 112 is a solenoid valve such as Ingersoll-Rand Solenoid Valve Model #CAT66P-120-A. Other activatable valves may be used. The second end of valve 112 connects to filter 114 through tube 122.

Filter 114 is a multilayer filter, containing layer 115 for odor absorption and layer 117 for particle absorption. Odor absorption layer 115 contains activated charcoal and the particle absorption layer 117 is a ULPA filter. Filter 114 contains RFID tag 118. RFID tag 118 is a passive RFID tag containing embedded information indicating the filter type and lifetime. RFID transceiver 119 is arranged within the housing and oriented to read RFID tag 118. RFID transceiver 119 is a Melexis part #MLX90109 RFID transceiver, however, other RFID transceivers may be used.

Controller 116 is an Alterra Stratix FPGA, however, other FPGA's, microcontrollers, CPUs, or logic devices may be used. Controller 116 contains embedded software which controls the operation of controller 116. Controller 116 receives input from line 123 which is connected to output 125 of receiver 124. Controller 116 contains an internal timer.

Receiver 124 is a current sensor having output 125 and input 126. Receiver 124 has terminals 126 and 127. Terminal 127 is connected to external power supply 130 through wall socket plug 129 and terminal 126 is connected to power line 132. The voltage on output 125 is a function of the magnitude of the current passing through terminals 126 and 127. Receiver 124 is an isolated hall-effect sensor such as those offered by Allegro Microsystems, Inc. Alternative current sensors, such as a simple resistor voltage divider, may also be used. An analog to digital converter may need to be placed between receiver 125 and controller 116 depending upon the type of receiver and controller used. Receivers based on technology other than current sensors may also be used as will be described in the following embodiments.

Power line 132 connects to line 133, which passes out inlet port 106 and travels within tubing 105 to medical apparatus 110. Line 132 and 133 contain multiple wires including at least a ground wire and a power wire. In the following example, medical apparatus 110 is an electrosurgical device. Medical apparatus 110 contains activation button 111 for turning on the electrosurgical device.

First Embodiment Operation

The operation of first embodiment 100 begins with properly connecting the embodiment to power supply 130, vacuum source 108, and medical apparatus 110. Wall socket plug 129 should be inserted into standard electrical wall outlet. Tubing 103 should be connected to outlet port 104's adapter and vacuum source 108, ensuring that an air-tight seals are created. Tubing 105 similarly should be connected to inlet port 106's adapter and the suction port on medical apparatus 110. Also, line 133 should be connected to the power line 132 and medical apparatus 110.

After all the proper connections are made, the medical apparatus should be off (activation button 111 should not be depressed). Since the medical apparatus is not on, there will be no current flow through lines 129 and 132. The lack of current flow will be sensed by current sensor/receiver 124 and indicated on output 125. Controller 116 will read output 125 and determine that the medical apparatus is not on. Controller 116 will then send a command signal along control line 141. Activatable valve 112 receives the control signal along line 141 and shuts the valve closed. With valve 112 closed, fluid flow is prevented along the path from medical apparatus 110, into inlet port 106, through filter 114, through valve 112, out outlet port 104, and to vacuum source 108.

When a user of medical apparatus 110 depresses activation button 111, medical apparatus begins to draw current along line 133 and thus along lines 132 and 129. Current sensor/receiver 125 senses the increase in current flow through terminals 124 and 126, and thus changes output 125. Controller 116 senses the change in signal on line 123 and in response changes the command signal on command line 141 from a closed signal to an open signal. Valve 112, in response to the open signal opens. Fluid is now allowed to flow from medical suction apparatus 110, and into inlet port 106. Impurities such as smoke particles and odors in the fluid coming in inlet port 106 are removed by filter 114. Fluid flow continues through valve 112, out outlet port 104 and into vacuum source 108.

Other Embodiments

Figure 2:
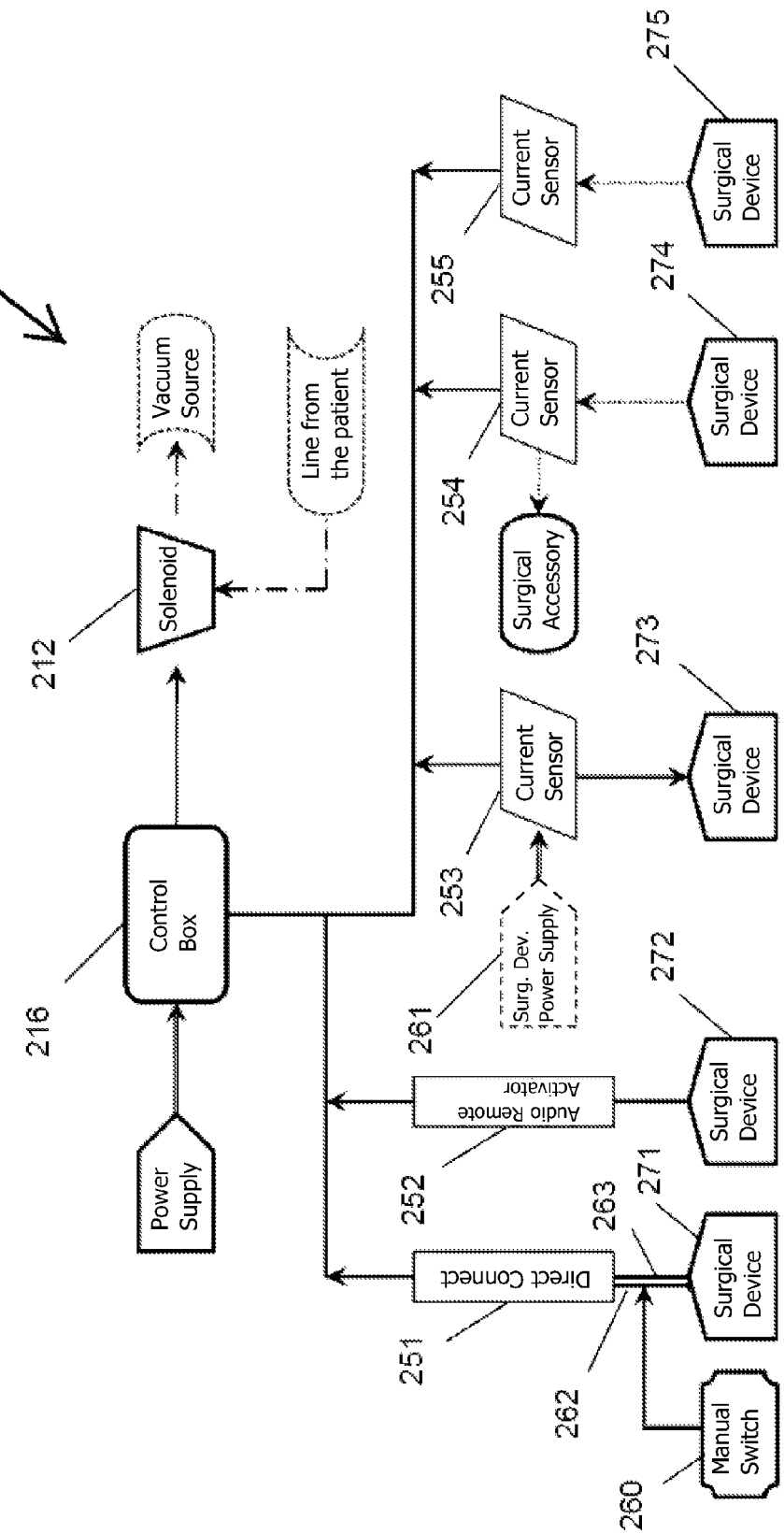
FIG. 2 shows a schematic view of a second embodiment.

FIG. 2 discloses second embodiment 200 which contains multiple receivers, 251, 252, 253, 254, and 255, designed to work with various surgical device types 271, 272, 273, 274, and 275. The multiple receivers allow for remote control to be accomplished in several different ways.

Receiver 251 is an adapter giving a direct electrical connection to manual switch 260 or surgical device 271. For example, manual switch 260 may be a foot pedal switch. Similarly, surgical device 271 may include manual switch buttons. Manual switch 260 and the manual button in surgical device 271 will electrically connect control wires 262 and 263. This electrical connection notifies the control box when the activation button on surgical device 271 or manual switch 260 are depressed and controls solenoid valve 212 accordingly. Alternatively, the manual switch or surgical device buttons may be analog switches which control an analog voltage level on line 263. In another form, the manual switch or surgical device buttons may provide a serial digital signal indicating their state on line 262.

Receiver 252 is an audio receiver such as a microphone. Surgical device 272 emits a fixed frequency tone when in use. Control box 216 contains a microprocessor for analyzing the microphone signal from receiver 252. Whether surgical device 272 is on is determined by analyzing the microphone signal. More specifically, a fast fourier transform is performed on the microphone signal. If the power within the frequency range containing the tone frequency emitted by surgical device is above a threshold, surgical device 272 is determined to be on and valve 212 is controlled accordingly. The threshold may be adjusted to minimize false activations. Additionally, DSP processors and advanced algorithms such as FIR and IIR filters may be used within the control box to more accurately trigger off of surgical device 272.

Receiver 253 is a current sensor connected to surgical device 273's power supply 261. Receiver 253 contains an output indicating the magnitude of the current drawn by surgical device 273. Control box 216's microprocessor compares the current level from current sensor (receiver) 253 and if determines if surgical device 273 is on based on whether the current sensor output exceeds a threshold. Multiple thresholds are used to detect multiple activation schemes of surgical device 273 and to adjust valve 212 accordingly. For example, surgical device 273 may be an electrosurgical device having a cut mode and a coagulate mode, each drawing different levels of current. A threshold may be created for each mode, and valve 112 assigned a separate flow rate for each mode.

Receiver 254 is a current sensor which operates without direct contact. Such current sensing is achieved using a halleffect sensor or a sensor containing an electrical loop around the surgical device power line. Similar to the operation of receiver 253, depending upon the magnitude of the output from current sensor 254, control box 216 will appropriately adjust valve 212.

Receiver 255 is an RF sensor configured to measure an AM signal in the frequency range of 350 kHz to 1.25 MHz. RF sensor 255 may be coupled to an antenna. Receiver 255 is configured to detect the RF given off by surgical device 275 when in operation. For example, an electrosurgical device typically gives off amplitude modulated radio signals in the range of 350 kHz to 1.25 MHz. Control box 216 can perform signal analysis on receiver 255's output similar to the analysis performed on audio receiver 252's output. RF mixers may be used to convert the RF signal to a lower (baseband) frequency range which can be more easily analyzed by the microprocessor within control box 216.

Figure 3:
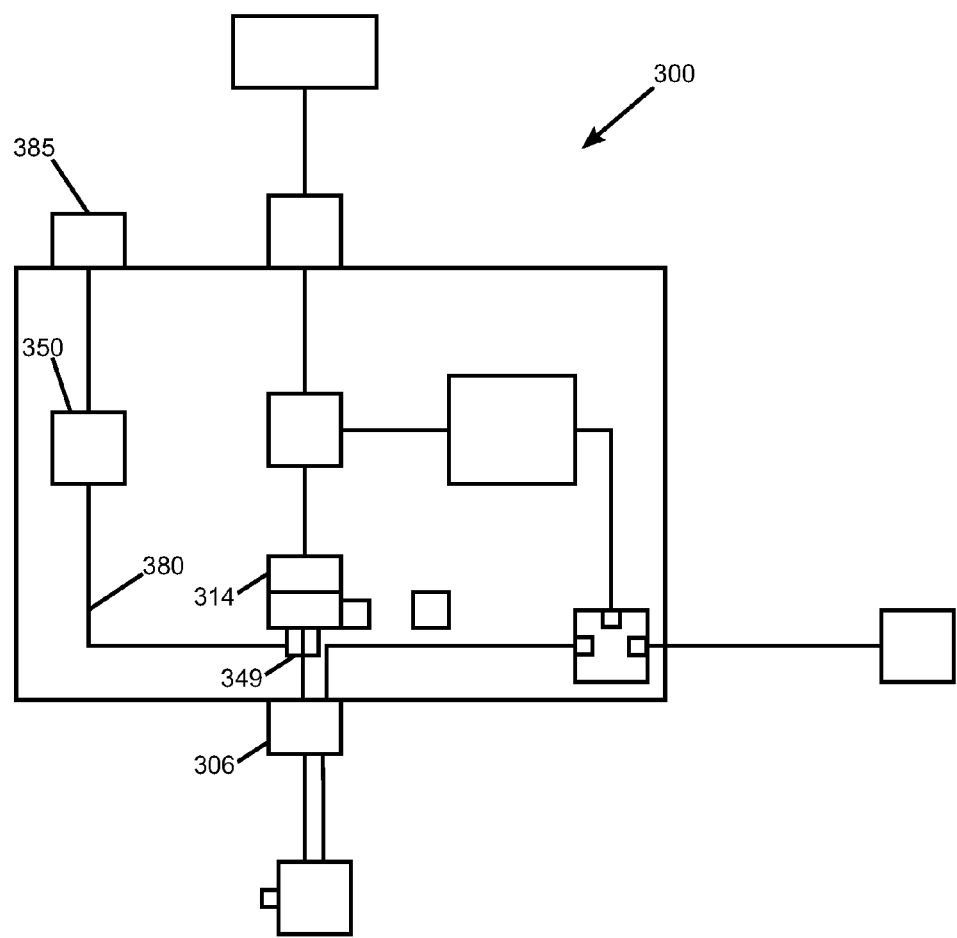
FIG. 3 shows a schematic view of a third embodiment.

In FIG. 3 third embodiment 300 is shown. Embodiment 300 is similar to embodiment 100 but includes flow splitter 349 and fluid canister 350. Flow splitter 349 is configured to separate any liquid entering inlet 306 into liquid path 380. The alternate path for gas should be free of any liquid. Flow splitter 349 may be part of filter 314. Fluid canister 350 may optionally be connected to liquid outlet port 385 which connects to an external liquid drain.

In other embodiments, a delay may be added to before switching the activatable valve open or closed from when the surgical device turns on and off. Additionally, a biohazard sensor may be added to any of the embodiments and may connect to an alarm. The filter may be designed to remove moisture. Additionally, an occlusion sensor may be added in the flow path and configured to cause the controller to shut the valve if an occlusion is detected. For example, if the suction device were to come into direct contact with flesh. Swivels may be added to the tubes. The device may be made of disposable or recyclable components. Additionally, the device may contain its own vacuum unit.

Figure 4:
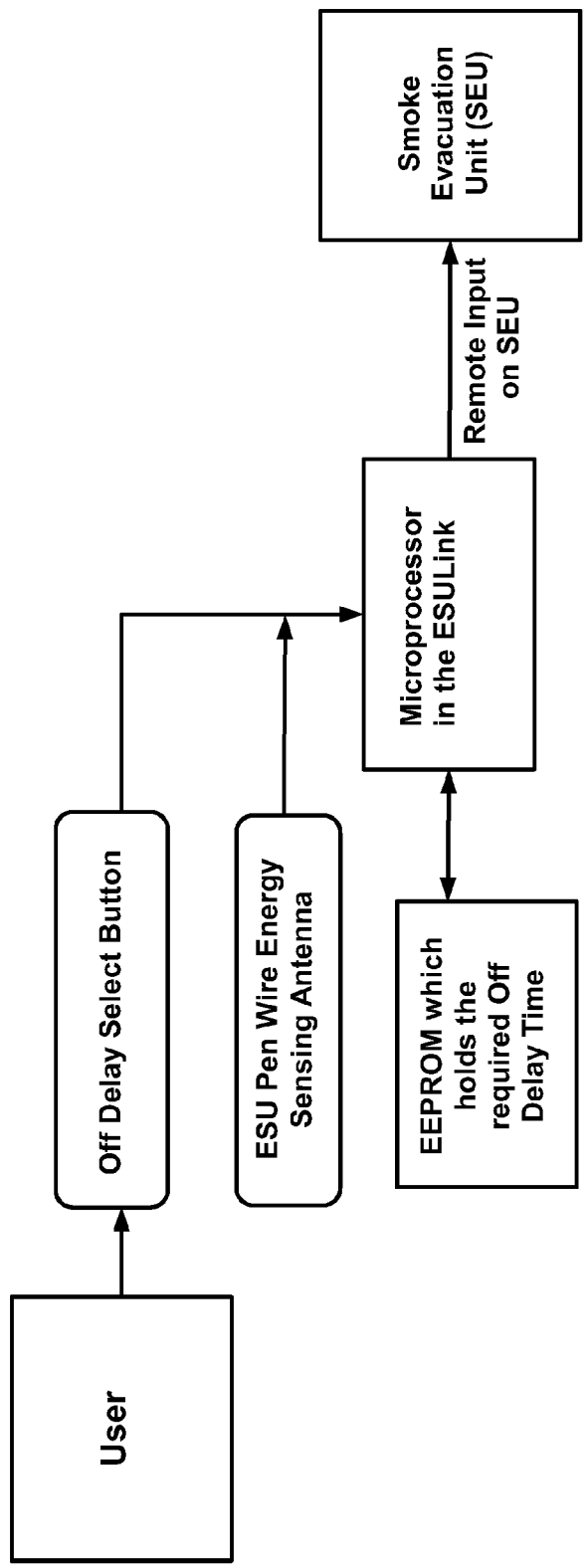
FIG. 4 is a layout of a fourth embodiment remote control unit accessory.

In FIG. 4, a fourth embodiment of a remote control unit is shown. The fourth embodiment provides a remote control unit in an accessory format that can be used to remotely switch on and off any device through a controlled output wire. As shown in FIG. 4, a smoke evacuator unit is the controlled device, receiving the output wire from the remote control unit. The fourth embodiment contains an RF sensor which is optimized for sensing the RF given off by an electrosurgical unit (electrosurgical pen). A user interfaces with the remote control unit in order to set a variety of operating parameters.

Figure 5:
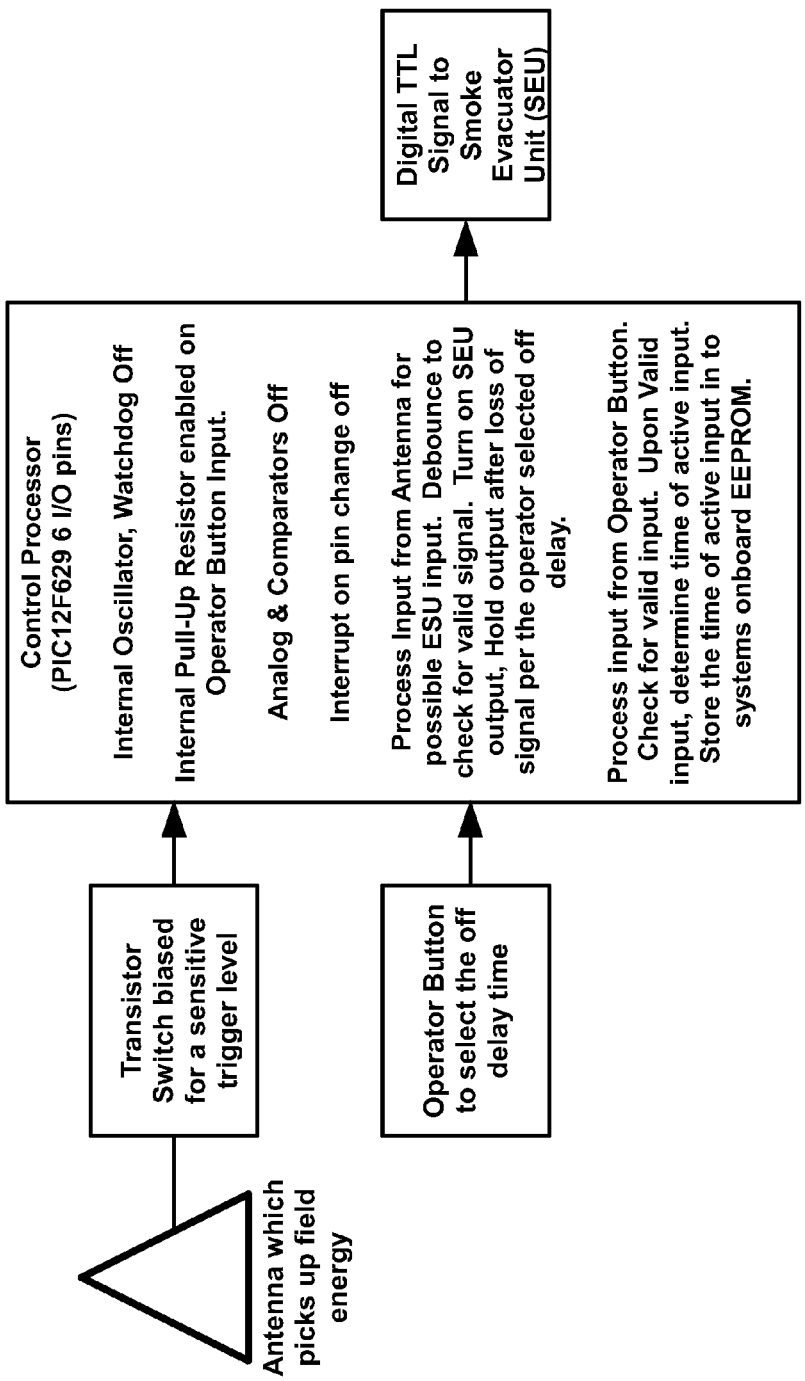
FIG. 5 is a high level circuit schematic of the embodiment shown in FIG. 4.

FIG. 5 shows the major circuit elements of the remote control unit, including an RF antenna, an amplification transistor, a user button, a microcontroller, and the control output line. The RF antenna is embedded into a printed circuit board. The transistor is properly biased with a voltage divider such that an RF signal sensed by the antenna is amplified at the microcontroller input pin. Software is provided on the microcontroller which samples the amplified RF input from the transistor and sets the control output voltage as a function of the input signals and several configuration parameters.

Figure 6:
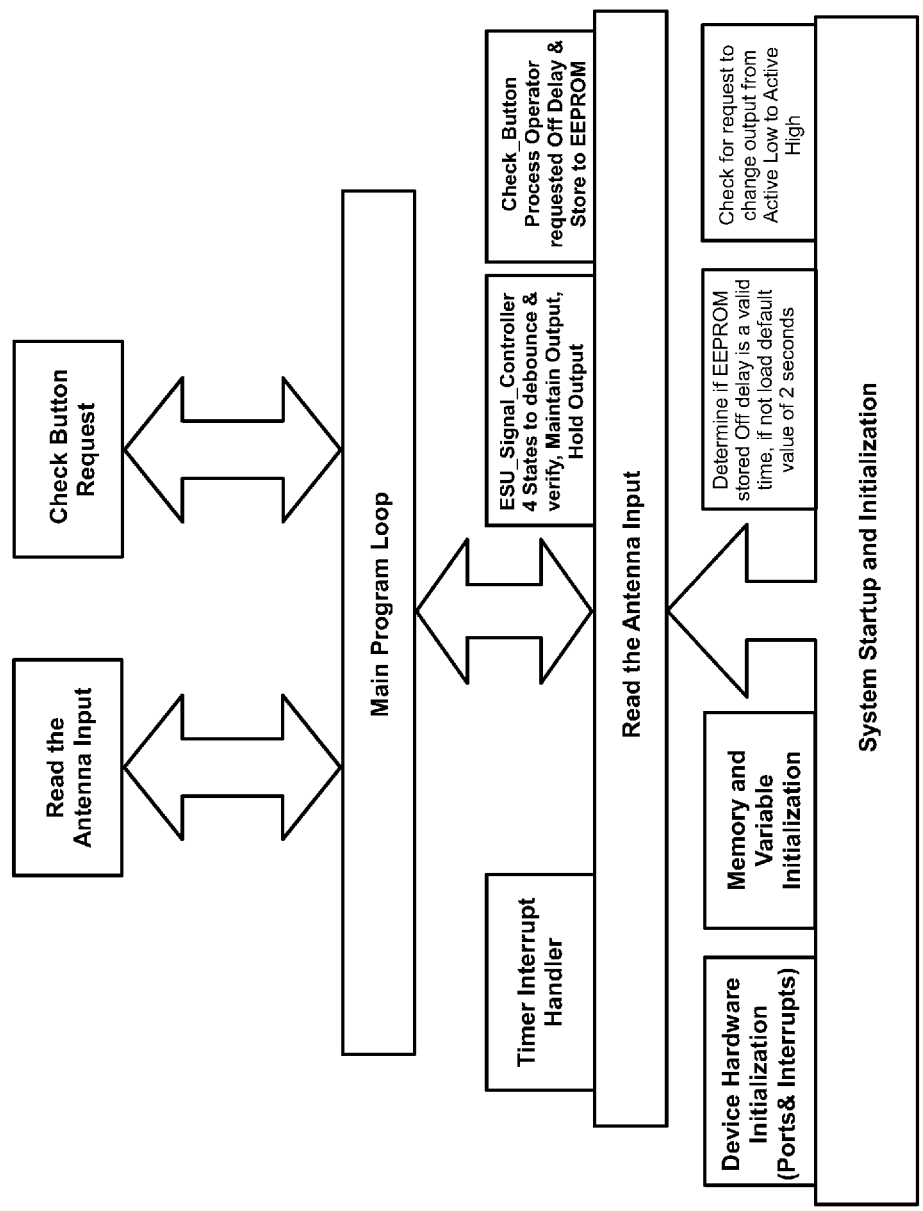
FIG. 6 is a high level software block diagram of the software running on the microcontroller shown in FIG. 5.
Figure 7:
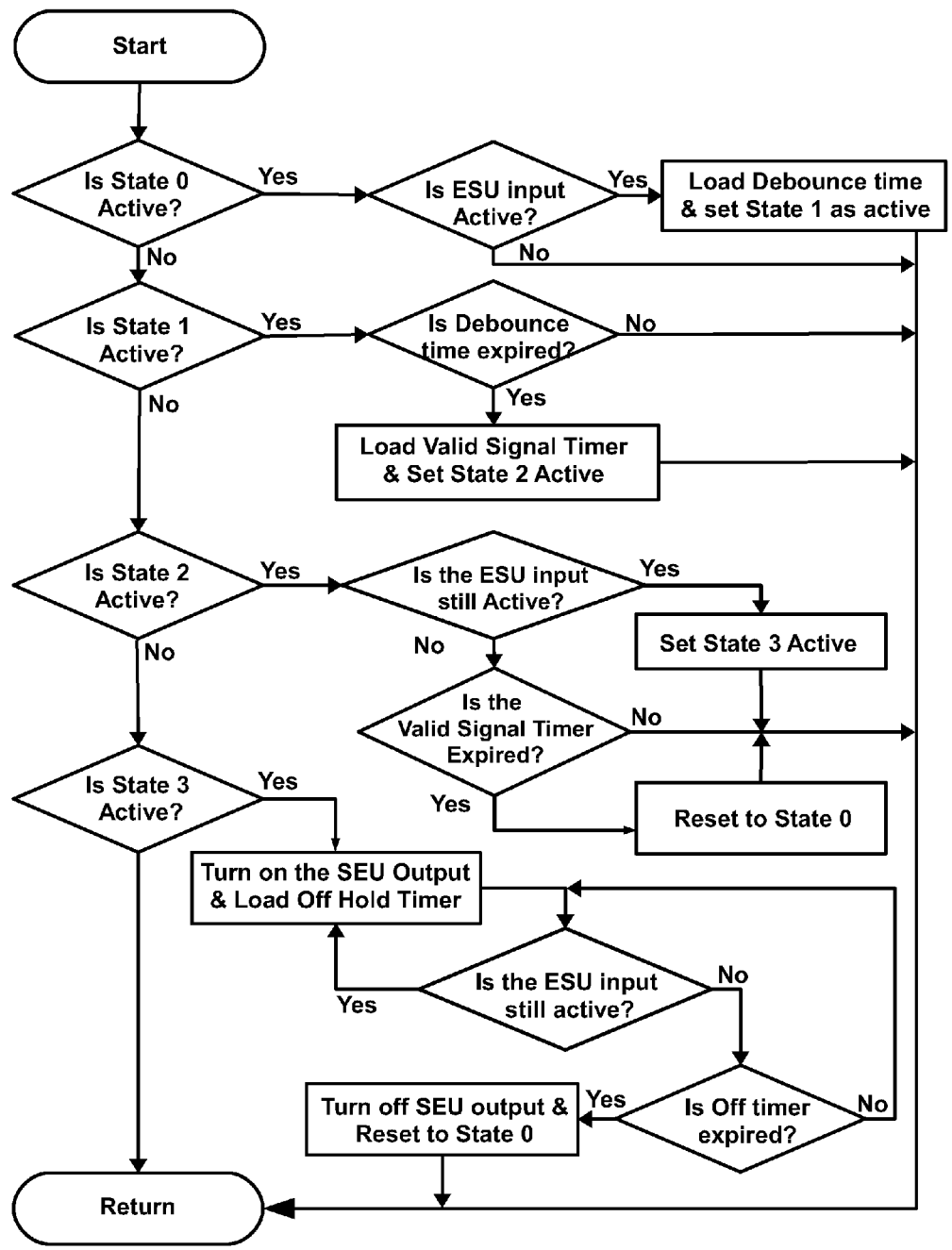
FIG. 7 is a state diagram of a software debouncing module in the fourth embodiment.
Figure 8:
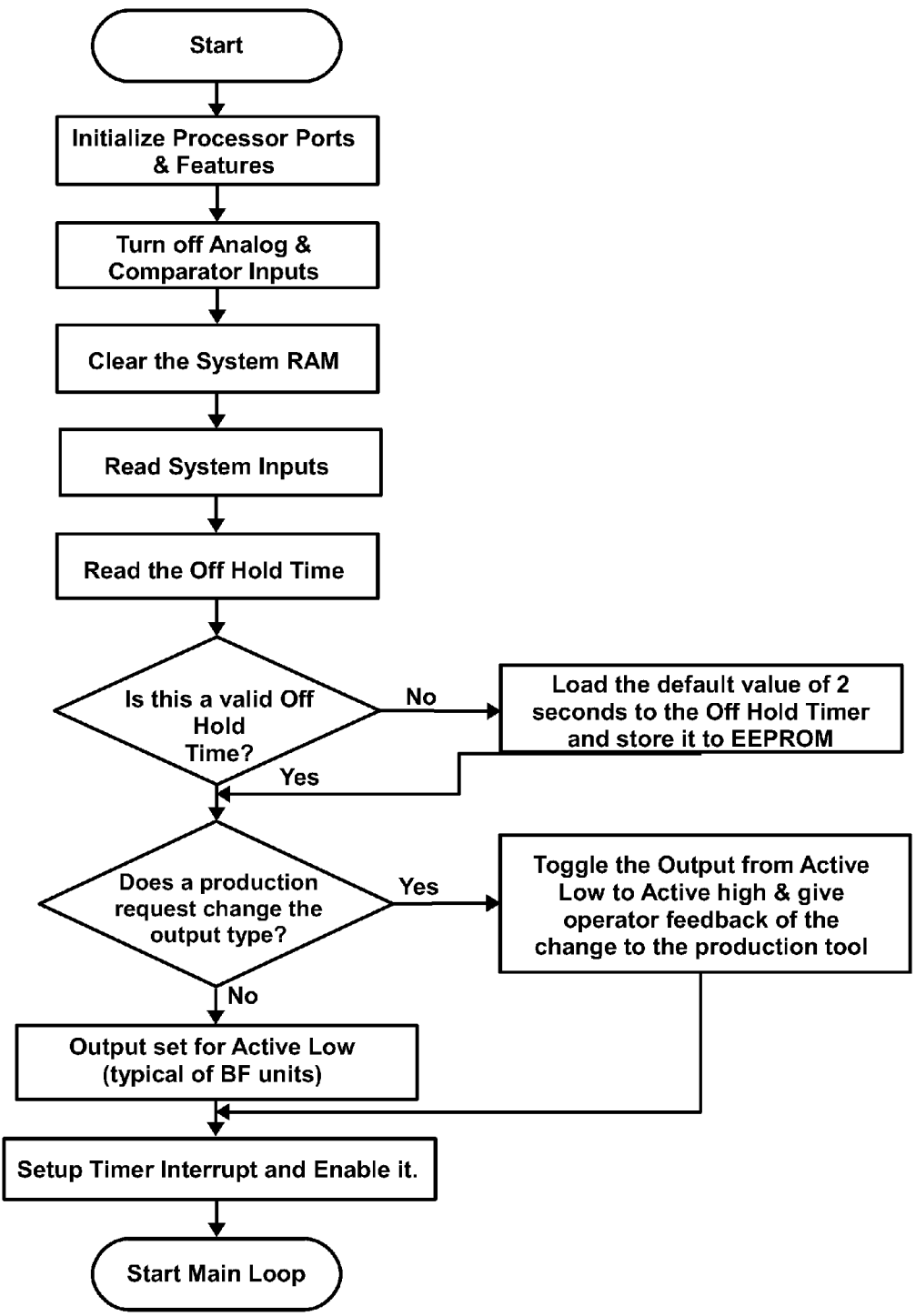
FIG. 8 is a perspective view of the embodiment in FIG. 4.

FIG. 6 is a top level software block diagram of the software running on the microcontroller. Several interrupt driven program subroutines are used. One subroutine periodically samples the RF input and another subroutine determines the user button state. In order to filter noise on the RF signal sensed from the antenna, a debouncing filtering subroutine as shown in FIG. 7 is used. More specifically, the debouncing routine follows the following steps.

The state machine starts in state A where the device begins searching for a low on the input. When a low is detected, a 100 mSec "debounce" timer is loaded and the state goes to state B.

In state B, the device first waits for the debounce timer to complete. When the debounce timer completes, an "Active Signal" timer for 200 mSec is set, and the state is then set to state C.

In state C, the device checks for an Active Low input. If the signal is still active low, the sensed signal is considered "on" and the state is changed to state D. Alternatively, if the signal is no longer active, the Active Low input is checked again, until the Active Signal timer has completed. If the Active Signal timer expires without ever sensing an active low, the state is changed back to state A.

In state D, the output is turned "on" by adjusting the voltage on the output line. An off delay timer (minimum of 100 mSec, user selectable to 10 Seconds) is set. The input is then repeatedly monitored. If the input is still active low, the state is reset to state D. If no active low signal is sensed and the delay timer is expires, the output is set to the "off" voltage, and the state is set to state A.

In summary, once the software detects a valid signal (and filters out noise) the ESU output is transitioned on, and left on until the software detects no signal for 100 mSec to 10,000 mSec (based on the user selected off delay time).

The described embodiments resulted in a number of unexpected results and advantages over the prior art. First, a device can be triggered off of the radio signals emitted by a surgical device. Such triggering allows the remote control device to be electrically isolated (no direct wire contact) from the surgical device. Such a configuration is advantageous to ensure that the electrical system of the surgical device is not compromised by external systems, thus increasing safety. Second, a remote activation device is provided which can be remotely triggered off of a variety of signal types. For example, when the surgical device the embodiment is used with provides a direct electrical connection for triggering the remote device, an adapter for receiving such signal directly is provided. Alternatively, if the surgical device emits an audio signal during use, this audio signal can be used to trigger the remote device. In other scenarios, the radio frequency radiation emitted by a surgical device can be used as a trigger. The described embodiments are reliable in that a low level of false triggering is attained.

Therefore, while the presently-preferred form of the method and device for a remote control unit has been shown and described, and several modifications discussed, persons skilled in this art will readily appreciate that various additional changes may be made without departing from the scope of the invention.

The invention claimed is:

1. A remote control system comprising:
   an electrosurgical device;
   a medical vacuum source configured and arranged to provide suction for removing surgical smoke generated by the electrosurgical device;
   a valve operatively associated with the medical vacuum source;
   a receiver having an output corresponding to the activation of the electrosurgical device;
   an output control line for controlling the valve;
   a controller, configured to store a threshold parameter into a threshold parameter storage, said threshold parameter being a function of said receiver output; and
   wherein said controller is configured to produce a signal on said output control line as a function of said receiver output and said threshold parameter storage.

2. A remote control system as set forth in claim 1 wherein said receiver is a RF receiver.

3. A remote system as set forth in claim 2, wherein said RF receiver is a Bluetooth transceiver.

4. A remote control system as set forth in claim 2, wherein said RF receiver is an IEEE 802.11b transceiver.

5. A remote control system as set forth in claim 1 wherein said receiver is an acoustic receiver.

6. A remote control system as set forth in claim 1 wherein said RF receiver may comprise an antenna.

7. A remote control system as set forth in claim 1 wherein said antenna is an integrated antenna.

8. A remote control system as set forth in claim 1 and further comprising a delay parameter.

9. A remote control system as set forth in claim 1 wherein said controller is configured to produce a signal on said output control line as a function of said delay parameter.

10. A remote control system as set forth in claim 9, and wherein said controller is configured and arranged such that when a threshold setting button is depressed, said controller sets said delay parameter as a function of a duration of time that said threshold setting button is depressed.

11. A remote control system as set forth in claim 1 and further comprising a logic level parameter used to designate whether a high voltage on said output control line designates an on or an off command to said device.

12. A remote control system as set forth in claim 1 wherein said controller is configured and arranged to debounce said RF receiver output.

13. A remote control system as set forth in claim 1 and further comprising a transistor for amplifying said RF receiver output.

14. A remote control system as set forth in claim 1 and further comprising a channel for retaining a current carrying wire.

15. A remote control system as set forth in claim 14 wherein said channel is configured to hold a plurality of wires.

16. A remote control system as set forth in claim 1, wherein the valve is a wall mounted valve disposed in fluid communication with the vacuum source.

* * * * *